United States Patent [19]
Morimoto

[11] Patent Number: 5,611,853
[45] Date of Patent: Mar. 18, 1997

[54] COMPOSITION OF MATTER AND SOLID MEDIUM BASED-ON NATURALLY-OCCURRING HUMIC ALLOPHANE SOIL USEFUL IN TREATMENT OF FLUIDS

[75] Inventor: Haruo Morimoto, 187, Nakajinzenji, Kochi-shi, Kochi-ken, Japan

[73] Assignees: Haruo Morimoto, Kochi-ken; Katusi Maeno, Tokyo; Takahiro Yamada, Osaka, all of Japan

[21] Appl. No.: 524,032

[22] Filed: Sep. 6, 1995

[30] Foreign Application Priority Data

Sep. 6, 1994 [JP] Japan .................................. 6-212431

[51] Int. Cl.$^6$ .................................. C04B 14/02
[52] U.S. Cl. .................. 106/633; 106/672; 106/605; 106/681; 106/706; 106/718; 106/793; 106/811; 106/284; 106/DIG. 7; 252/175; 210/348; 210/500.1; 524/442
[58] Field of Search ..................... 106/603, 633, 106/672, 681, 706, 718, 793, 811, DIG. 7, 284, 137, 209, 214; 252/175; 210/348, 500.1, 503; 524/445, 442

[56] References Cited

U.S. PATENT DOCUMENTS

| 4,256,728 | 3/1981 | Nishino et al. | 422/4 |
| 5,342,419 | 8/1994 | Hibbard | 51/308 |

FOREIGN PATENT DOCUMENTS 64-6838  2/1989  Japan .

*Primary Examiner*—Mark L. Bell
*Assistant Examiner*—Michael Marcheschi
*Attorney, Agent, or Firm*—Sughrue, Mion, Zinn, Macpeak & Seas

[57] ABSTRACT

A composition of matter comprising naturally-occurring humic allophane soil or Ando soil as an essential ingredient admixed with a binder material, said composition is useful in preparation of solid media effective as deodorant, absorbent, adsorbent and the like for treating fluids, in particular contaminated water and malodor air.

11 Claims, 2 Drawing Sheets

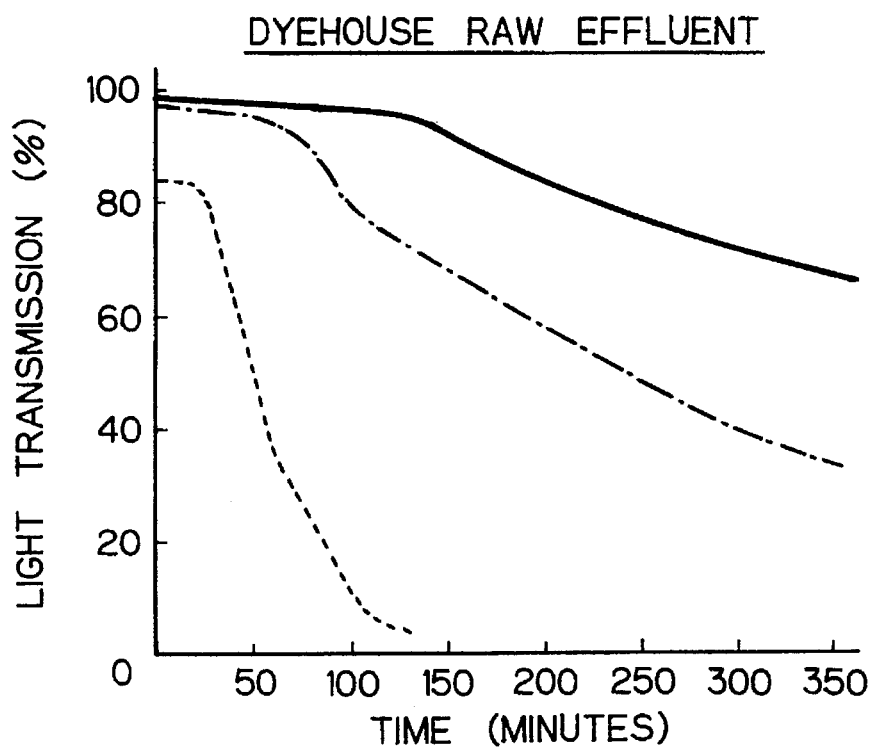
Fig. 3
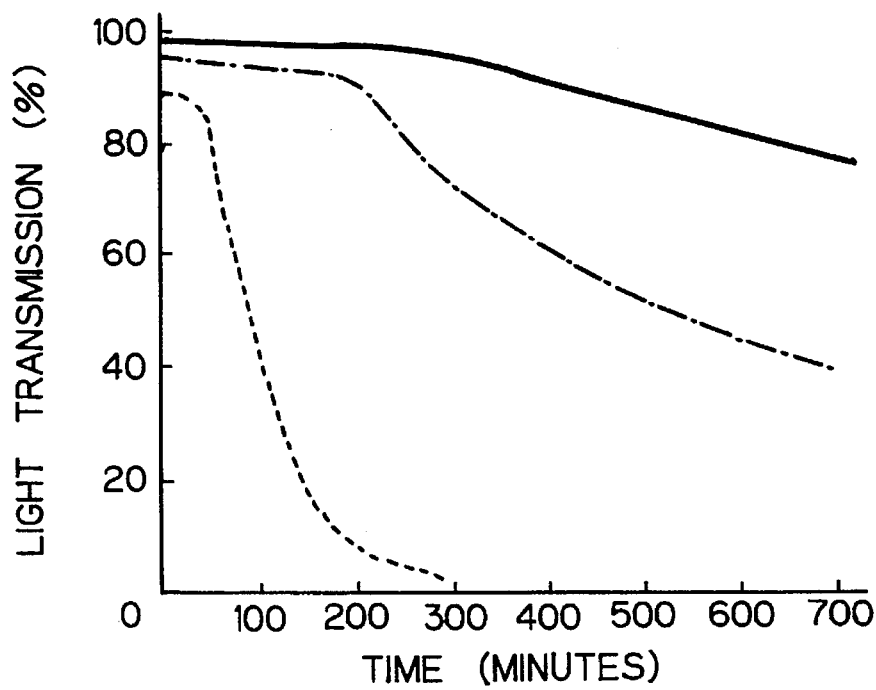

COMPOSITION OF MATTER AND SOLID MEDIUM BASED-ON NATURALLY-OCCURRING HUMIC ALLOPHANE SOIL USEFUL IN TREATMENT OF FLUIDS

FIELD OF THE INVENTION

This invention relates to a composition of matter for use in preparation of solid media for treating fluids, i.e., gases such as air, and liquids such as water, in particular waste water or sewage. Particularly, the invention relates to such a composition comprising essentially of naturally-occurring humic allophane soil particulates blended or kneaded with an organic or inorganic binder and, optionally, an aggregate material and/or additives such as an air entraining agent and a filler material. The composition may be converted, by any suitable fabrication or forming process, into various fluid treating media, such as air deodorants and water treating agents, which find a wide range of domestic and commercial applications. The present composition itself and treating agents prepared therefrom exhibit excellent performances in deodorization, decolorization, contaminant removal and the like, when contacted with streams of fluids.

PRIOR ART

The region of upper surface layer, "A" layer, of volcanogenous soil comprises a weathering product originating from the sedimented volcanic ash and is a heavily dark soil comprising an amorphous clay mineral, allophane, as a major component accompanied with a significant proportion of humic substances including, humic and fulvic acids. This mineral soil is often referred to as "Ando" soil. Herein, it will be referred to as naturally-occurring humic allophane soil, or humic allophane soil, or simply allophane soil.

It has been elucidated and reported by the pedologists that the allophane soil has actions such as. absorption, adsorption, exchange, buffer etc., on various species of substances, e.g., ions, compounds, complexes and the like, by virtue of the integrated result of the physical and chemical absorption-adsorption properties inherent to the allophane clay mineral and to the humic substances, respectively. The pedologists have utilized the properties for the purpose of fertilization of the allophane soil farmland.

However, it has been scarcely thought to utilize the special behaviors or properties of the humic allophane soil in any applications in the fields other than the field of pedology or agriculture, for example for purposes of deodorization, decolorization and the like.

Japanese Patent Publication (KOKOKU) No. SHO 64-6838 describes a lumpy solid agent for clarification of water which comprises "Ando" soil originating from volcanic eruptives and containing mainly allophane mineral and humic acids, said soil being mixed with volcanic ash and active carbon and bound by a binder onto a matrix that are porous volcanic detritus (i.e., pumice) containing numerous pores of various sizes. It is said that both the volcanic ash and the active carbon should be added in order to enhance and improve the adsorption and other properties of the Ando soil. It is also said that the powdery Ando soil as such has poor handling properties to be used in purification of water, that the handling properties are improved by binding the powdery soil together with the other ingredients onto the surface and into the pores of the matrix, pumice stone, and that the thus resulting Ando soil/volcanic ash/active carbon/pumice composite solid structure is one of the most important features of the water clarifying agent disclosed in said Japanese Patent Publication.

The known water clarifying agent has typically a composition of the essential ingredients as follows:

| | |
|---|---|
| 15–40 parts | Ando soil |
| 15–35 parts | active carbon |
| 20–70 parts | volcanic ash | per 100 parts of crushed volcanic pumice stone matrix (on the volume basis).

Of the essential ingredients, the volcanic detritus (pumice stone), the Ando soil and the volcanic ash are available from the natural resources and are made usable in the production of the water clarifying agent after simple purification, respectively. Though the remaining ingredient, active carbon, is one of the most commonly used deodorants, the active carbon, however, should be artificially synthesized from botanical materials and are considerably expensive as compared with the above three naturally occurring ingredients. The active carbon may be commercially prepared, for example, by the steam-activation and zinc chloride-activation processes. However, in Japan, it is difficult to obtain the good botanical materials suitable for preparing the active carbon, and the production of active carbon relies largely upon the botanical materials, such as palm shell, imported from the tropics.

Therefore, though the active carbon is an essential ingredient for the above-mentioned water clarified agent, if it is possible to omit the expensive active carbon ingredient from the water clarifier agent that contains the active carbon in a substantial proportion and is consumed in a relatively large quantity, an inexpensive water clarifier agent could be provided and the clarification of water could be effected at a reduced cost.

Accordingly, I, the inventor, have tested the deodorization and decolorization performances of the active carbon in comparison with those of the naturally occurring humic allophane soil to obtain the conclusions that the active carbon is capable of adsorbing only for a relatively short period of time, small quantities of odorous and coloring substances from the fluids under being treated therewith, and that the active carbon is unsuitable for applications where prolonged deodorization and decolorization performances are required, as in the deodorization of indoor air or the treatment of effluent or sewage water. Thus, when the active carbon is used as an adsorbent in a contaminated fluid, such as air or water, its saturation point is rapidly attained as small quantities of odorous and coloring substances are taken up from the fluid, and consequently its adsorptivity is seriously reduced. Rather it can be often observed that the once taken-up odorous and coloring substances are released from the saturated active carbon adsorbent to re-contaminate the treated fluid. Further it has been found that the active carbon has deodorization and decolorization capacities (i.e., saturation points) substantially lower than those of the humic allophane soil. Thus, contrary to expectation, it has been found that the service life of the known water clarifying agent is rather shortened as a whole due to the presence of the active carbon ingredient. On the basis of the knowledge obtained from the above comparative tests, the inventor has been convinced that omission of the active carbon ingredient from the composition of the above-mentioned prior art water clarifier agent will result in a prolonged stable adsorptive performance as well as a reduced production cost.

Furthermore, the inventor has attempted to omit the matrix, i.e., volcanic detritus and also the volcanic ash as much as possible or even completely from the composition of the above-mentioned prior art water clarifier agent so that the deodorization and decolorization capacity per unit volume or weight is enhanced and hence the volume or weight of the agent consumed is decreased. Thus, it has been realized that the volcanic detritus and ash ingredients need to be used only in reduced proportions or even may be completely omitted except for the case where the respective particles or lumps of the clarifier agent must have a high structural integrity or adhesion strength, or alternatively a high physical strength, such as compression strength, as in an application in which the clarifier agent is employed for treating a massive stream of water.

When the allophane soil is employed for deodorizing a gaseous stream, such as of air, the soil is applied onto a web material such as paper, woven fabric, felt, nonwoven fabric, sponge sheet, other porous sheet and the like and then a stream of gas to be treated is passed through the soil-loaded web. In this case, it is preferred to use no coarse particles, such as of volcanic detritus (i.e., pumice) together with the allophane soil.

When the clarifier or treatment agent is exhausted out or the service life expires, it has to be disposed, for example, as a landfill material. If the clarifier or treatment agent contains volcanic detritus particles in a large proportion as taught by the above-mentioned Japanese KOKOKU specification, a correspondingly increased volume of the waste agent may present a further problem in disposal particularly in shipping thereof. With this regard, a decreased proportion of volcanic detritus used in the clarifier agent is desirable.

SUMMARY OF THE INVENTION

Accordingly, a primary object of the invention is to provide a naturally-occurring humic allophane soil-based composition which is ready-to-use in preparation of agents for treating fluids, i.e., gases and liquids. With the agents, the fluids are efficiently treated utilizing fully the excellent absorption/adsorption properties of the naturally-occurring, readily available allophane soil.

The invention provides various forms of treatment agents that are prepared from the allophane-based composition and have an extended period of service life. The invention provides also various fashions of use of the treatment agents.

Thus, the invention provides a composition of matter for use in preparation of solid media for treating fluids, which comprises naturally-occurring humic allophane soil as an essential ingredient admixed with a binder material.

BRIEF DESCRIPTION OF THE DRAWINGS

FIGS. 3 and 4 are similar to FIGS. 1 and 2, where a raw effluent water from a dyehouse was treated, respectively.

DETAILED DESCRIPTION OF THE PREFERRED EMBODIMENTS

Figure 1:
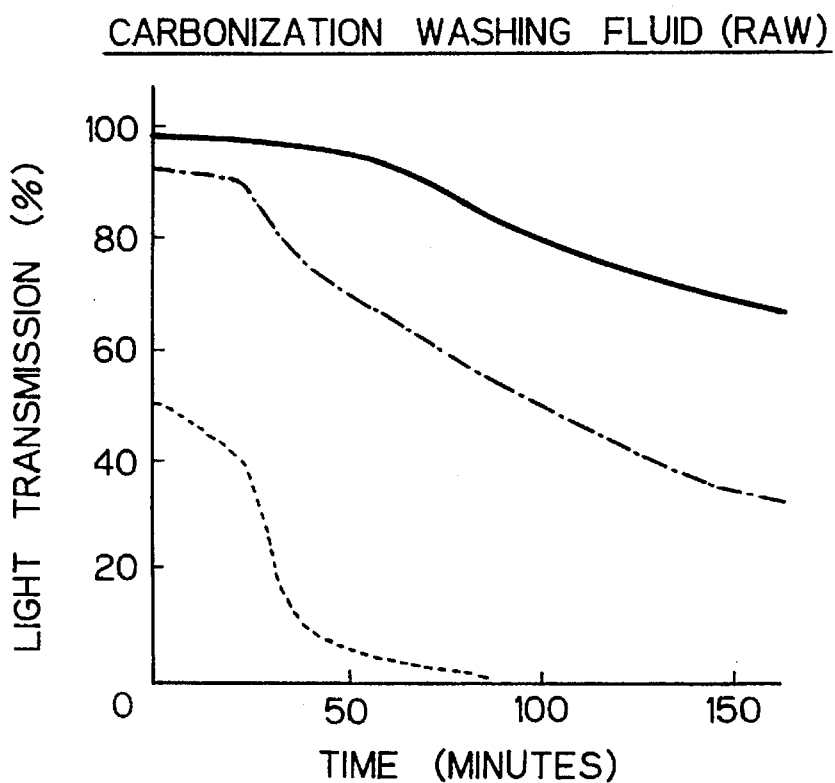
FIG. 1 is a graphic presentation of light transmission % of a raw effluent water from a metal work factory, treated by an agent according to the invention (the solid line), an agent of Japanese KOKOKU No. SHO 64-6838 (the chain-like line) or a commercially available active carbon (the broken line), for a period of up to about 150 minutes.

The composition according to the invention may be formulated as a paste having an appropriate consistency, which is then formed or shaped into a suitable form of particulate or lumpy solid and dried or hardened to give a fluid-treating media or agent. Alternatively, the composition may be formulated as a liquid suspension which is applied to or impregnated into a porous substrate and dried or hardened to give a fluid-treating media.

The principal ingredient, naturally-occurring humic allophane soil, of the present composition is readily available from the surface layer (i.e., "A" layer) of weathered volcanic ash soil that is widely and frequently deposited over a volcanic country Japan, but is not generally preferred from the agronomic viewpoint. The raw humic allophane soil material picked from such the resources is, preferably, dehydrated or dried by any suitable drying means, for example, by sun- and/or air-drying or by moderately heating; disintegrated and finely divided; and separated from any contaminative inclusions such as detritus and extraneous matters, e.g., botanical roots and remains, to give a refined humic allophane soil product. The thus dried and finely divided allophane soil itself tends to be scattered and to make a dust. The scattering properties are not convenient for handling and conveying the refined allophane soil. However, according to the invention, the refined allophane soil is mixed or diluted with a binder material which may be solid or liquid, and generally the scattering problem is significantly reduced or even completely solved. Thus, the subsequent handling, conveying, processing and other stages will not be seriously suffered from the scattering problem.

Typically, the composition of matter according to the invention comprises, on the weight basis:

| humic allophane soil | 40–80%, | preferably | 40–60% |
|---|---|---|---|
| binder material | 20–50%, | preferably | 30–50% |
| aggregate | 0–30% | | |

The binder material used in the composition may be any inorganic or organic binder and is selected depending on the particular final use of the treating agent or medium prepared from the composition. Where the agent or medium is to be used for treating water, the binder material is preferably an inorganic cement. Particularly preferred are a class of commercially available special cements or solidifying agents which have been developed for special civil engineering purposes, such as of stabilization of grounds and solidification of muddy grounds. Examples of such special cements include those available under the trademark "AUTOSET" from Autoset Corporation, "TOUGHROCK TL-L" from Sumitomo Cement Ltd , "ROCKMIGHTY W" and "SOLFIX" from Chichibu Cement Ltd., "SOLSTAR S" from Nippon Steel Corp., "ESC-R FLECON" from Osaka Cement Co., Ltd. and the like. For information, the above-mentioned "TOUGHROCK", a lime-based product, has a typical chemical composition as follows:

| ignition loss | 2.5% |
|---|---|
| $SiO_2$ | 4.2% |
| $Al2O_3$ | 1.1% |
| $Fe_2O_3$ | 0.6% |
| CaO | 73.9% |
| MgO | 2.0% |
| $SO_3$ | 1.6% |
| others | remainder |

"AUTOSET" No. 3100 has a typical chemical composition of:

| | |
|---|---|
| ignition loss | 0.3% |
| insoluble | 0.1% |
| $SiO_2$ | 16.1% |
| $Al_2O_3$ | 12.3% |
| $Fe_2O_3$ | 2.4% |
| CaO | 57.6% |
| MgO | 0.7% |
| $SO_3$ | 10.3% |

The conventional Portland cements have an approximate composition of about 20–30% $SiO_2$, about 4–6% $Al_2O_3$, about 2.5–4.5% $Fe_2O_3$, about 63–66% CaO, about 1–2% Mg and others.

As seen from the above, the class of special cements used for stabilizing and solidifying the soil ground and mud are modified in their chemical compositions as compared with the conventional Portland cements. Where the composition of the invention is used as an agent or medium for treating water, preferably a binder having an alkalinity as low as possible, because if a high alkaline binder is used, the resulting treatment agent will give rise a very high alkaline pH in the water under treatment in the initial stage and it will take a considerably long period time to attain an approximately neutral pH in the water.

Other than the cements, inorganic binder materials such as lime and sodium silicates, i.e., so-called "waterglasses" may be used in the invention.

Examples of the organic binder materials which may be used in the invention include synthetic resins, such as thermoplastic and thermosetting resins, tars and pitches, arabic gum, gelatin, starch and starch derivatives and the like. These may be used in any suitable combination.

Where the treating medium or agent of the invention is to be used for treating a mass of water, for example, a gush of effluent, it is preferred to introduce an appropriate aggregate material to the composition so that the treating medium or agent prepared from the composition is improved in the physical and mechanical strength to well resist the hydrodynamic actions exerted by the stream of water for a long period. An example of preferred aggregates is volcanic detritus. Usually the volcanic detritus may be conveniently gathered in an area near to or the same as the area where the main ingredient humic allophane soil is picked. Further since the volcanic detritus, i.e., pumice stone, is very porous and will contribute to reduce the weight of unit volume of the treatment medium or agent prepared from the composition as well as will contribute to increase the surface area available for treatment by contacting with the water. For similar reasons, the volcanic ash also may be used advantageously as an aggregate material. Further, if desired, pieces or particles obtained by crushing bricks or aerated light concretes may be also used as aggregate. Of course, the commonly used aggregate materials may be used in accordance with the invention. However, the aggregate materials are preferably porous to contribute to lightweight of the product treatment media or agents.

It is possible, if desired, to incorporate an ARE (air entraining) agent or other foaming agent to the composition to increase the contact surface area and to decrease the weight per unit volume of the product agents or media.

The compositions of the invention may be converted into fluid treating media in various manners depending on the particular formulations thereof. Some typical examples of the preparation will be illustrated below:

(1) Preparation of a sheet-like medium for gas-treatment

A uniform mixture was prepared by blending 75 parts by weight of dried humic allophane soil with 25 parts by weight a starch binder. Into this uniform mixture (100 parts by weight), 220 parts by weight of water was slowly added to produce an aqueous suspension with stirring while warming to about 60° C. The starch was gelatinized. Part of the warmed aqueous suspension was used to coat a surface of paper sheet which was then dried in a stream of air at around 55° C.

The resulting allophane soil-coated paper sheet shows an excellent deodorant effect when it contacts with a stream of malodor gas. This product will find its application as a wall paper or its equivalent for wardrobe closet, rest room, kennel, pet room or the like.

Though a paper sheet was coated with the allophane soil suspension in the above embodiment, other web or substrate materials such as fabric, nonwoven fabric, glass fiber cloth, glass fiber mat, mineral fiber cloth, chip board, particle board or the like may be coated or impregnated with the allophane soil suspension to give various deodorant products.

(2) Preparation of a bulky medium for gas-treatment

Part of the aqueous allophane soil/starch suspension from the above preparation (1) was used for impregnating a mass of absorbing cotton wool. The cotton wool was thoroughly dried.

The resulting allophane soil-loaded cotton wool may be packed in a duct. Where a stream of an odorous gas such as air is passed through the duct, there will be an effective deodorization caused.

In place of the above-used absorbing cotton wool, any other porous or permeable materials, such as glass wool, mineral wool, rock wool, metallic wool, wood (e.g., lumber), particle board, sponge, urethane foam and the like may be used. However, a suitable binder, for example, a resinous binder, should be chosen depending on the nature of the supporting material to be used. Further, instead of the water, any suitable suspending medium, for example, an organic solvent, may be used.

(3) Preparation of a granular agent for treating fluids

Humic allophane soil 60 parts by weight and a commercially available solidifying agent (Autoset No. 3100) 40 parts by weight were mixed uniformly in a mixer. Into the mixer, 20 parts by weight of water was slowly added and mixed to produce an aqueous paste, which was then extruded through a multi-orifice die (each orifice having a diameter of 3 mm). The extruded lines were allowed to dry and harden. The solidified extrudates were gently crushed to give a granular product having a mean length of 18 mm, the diameter being about 3 mm as original.

The resulting granular product may be packed as a bed or layer in a column, duct or the like. A stream of a contaminated fluid, e.g., water or other liquid may be passed through the packed column to leave the column as a clarified stream.

Though the extrusion method was used in the above case, any other suitable technique, for example, tableting, rolling, pressing or other granulation technique also may be used. The product may be in the form of beads, rings, saddles, bars, tubes, cylinders, discs, rings, honeycombs or other regular or irregular shapes.

(4) Preparation of a mechanically strengthened water-treatment medium

In this embodiment, the mechanical strength of water-treatment medium is increased so that the medium can well resist to high hydrodynamic pressure and other forces, impaction and shock which may be encountered where the medium is used for treatment of a mass of water.

Humic allophane soil 45 parts by weight and a commercially available solidifying agent (Autoset No. 3100) 25 parts by weight were mixed together with an aggregate material comprising 30 parts by weight of crushed volcanic detritus (size distribution about 2–33 mm; mean diameter 27 mm) in a mixer. Further, 23 parts by weight of water was added to the mixture which was then kneaded. The resulting aqueous mixture was discharged from the mixer and spreaded in a depth of about 150 mm over the top of a vibration plate which was mechanically vibrated at about 7–11 Hz for a period of about 70 minutes while compacting and densifying the mixture and allowing the mixture to moderately harden.

The resulting solidified block was broken into lumps having a size range of about 20–140 mm and an average diameter of approximately 130 mm. The product is suitable for use in treatment of a mass of water, such as industrial and densitic effluents.

Though the aqueous mixture was formed by spreading it on the vibration late in the above embodiment, it is also possible to extrude the mixture into a cylindrical extrudate or any other extrudate having a polygonal cross-section, cut the extrudate into segments having an appropriate length, and dry and harden the segments.

Further it is possible to press-form the aqueous mixture in an appropriate mold cavity.

The water content in the aqueous mixture should be adjusted to obtain a suitable consistency for a particular forming method to be employed.

Though the above-prepared lumpy product had an average diameter of about 130 mm, the diameter of the product may vary broadly, for example, in the range of about 1 mm to about 200 mm. If a solid treatment medium having a small particle size is used for treating a large amount of water at a relatively high space velocity, the small particles can be lost seriously due to entrainment into the exiting stream during the treatment process.

As aforementioned, the present invention relies largely upon the inventors findings that, with respect to deodorization, the humic allophane soil behaves very differently from the active carbon. This will be experimentally exhibited below.

Deodorizing test 1

In a series of experiments, each of the allophane soil and three commercially available household active carbon deodorant products (abbreviated as K, N and A, respectively) was tested organoleptically for diminishment of the offensive odor of ammonia.

Each of the samples, 5 g, was wrapped in a piece of permeable paper sheet and suspended by means of yarn in a wide mouth bottle of a 500 cc. capacity. A 28% aqueous ammonia solution was added in aliquots into the bottle from time to time while organoleptically monitoring the malodor of the gas phase in the bottle as set forth in Table 1. The sensory test results are also given in Table 1.

TABLE 1

| Passage of time (mins.) | Aqueous ammonia added (ml.) | Sensed intensity of ammonia odor | | | |
|---|---|---|---|---|---|
| | | Active carbons | | | Allophane soil |
| | | K | N | A | |
| 0 | 1.0 | strong | strong | moderate | weak |
| 5 | | " | " | weak | very slight |
| 15 | | " | " | slight | not sensible |
| 20 | 1.5 | (no longer effective as deodorant) | (no longer effective as deodorant) | very slight | " |
| 80 | 1.0 | | | not sensible | " |
| 900 | 1.0 | | | " | " |
| 1005 | 1.0 | | | " | " |
| 1905 | | | | " | " |

Deodorizing test 2

Dried humic allophane soil 500 g and a commercially available household deodorant A for refrigerator 500 g were charged each in a sealed box (7 cm×7 cm×17 cm). Into the box, 3.5 ml of a 28% aqueous ammonia solution was injected. The box was allowed to stand. A sample of the gas phase was taken from the central portion of the box from time to time and analyzed for the ammonia nitrogen content. The determined ammonia nitrogen concentrations in the gas phase are represented in Table 2 as percentage values calculated on the basis of the initial concentration (=100%).

TABLE 2

| Time (mins.) | Humic allophane soil | Active carbon-A |
|---|---|---|
| 0 | 100 | 100 |
| 5 | 49 | 100 |
| 15 | 21 | 98 |
| 20 | 2 | 99 |
| 80 | 1 | 97 |
| 900 | 0 | 97 |

The results of the two test show that the allophane soil is much more effective in deodorization (adsorption) than the commercially available active carbon deodorants for household refrigerator. Therefore, if the allophane soil is used in combination with such an active carbon, the excellent adsorption characteristics of allophane soil will be weakened.

The invention will be further illustrated with reference to the following non-limiting Examples.

EXAMPLE 1

Sample of the granular product from the above "(3) Preparation of a granular agent for treating fluids" was packed in a cylinder having an inner diameter of 50 mm and an effective length of 300 mm. A stream of air contaminated with 50 ppm $H_2S$ was continuously passed at a constant space velocity of 9.5 $hr^{-1}$ through the packed agent in the cylinder, while monitoring the exiting gas stream with a continuous gas analyzer with a sensitivity of 0.5 ppm for $H_2S$ until any $H_2S$ was first detected in the exiting gas stream after 2 days and 7 hours from the start (breakthrough time).

With the purpose of comparison, the above procedure was repeated using the same quantity of a commercially available active carbon deodorant "A" in place of the granular agent of the invention. The break-through time was only 4 hours 13 minutes.

EXAMPLE 2

Samples of the lumpy product from the above "(4) Preparation of a mechanically strengthened water-treatment medium" (particle size range of about 10–30 mm; specific surface area of about $4.0\times10^3$ m$^2$/l) were evenly graveled all over sections of the stream beds of water streams running in public gardens A and B, respectively. At the upstream end (raw water) and downstream end (treated water) of the graveled section in each of the gardens, the water was sampled and analyzed 5 times at approximately equal intervals for 3 months of the summer season (from June to August).

Though each of the analyzed items showed slight variations during the test period, generally the variations seemed negligible substantially. Therefore, the analysis results are set forth as three-month averages in Tables 3 (garden A) and 4 (garden B) below.

In the public garden A, the width of the water streamlet was 0.70 m and the mean flow rate was 370 m$^3$/hr. A section of 17.6 m length of the streamlet was graveled with 1.6 m$^3$ of the water-treatment medium.

In the public garden B, the width of the water streamlet was 1.80 m and the mean flow rate was 2,270 m$^3$/hr. A section of 19.4 m length of the streamlet was graveled with 4.5 m$^3$ of the water-treatment medium.

TABLE 3

| | (Garden A) | | |
|---|---|---|---|
| Analysis items | Raw water | Treated water | Average removal (g/m$^3$ · day) |
| pH | 7.0 | 7.2 | — |
| DO (mg/l) | 7.0 | 7.5 | — |
| suspended matters (mg/l) | 50.0 | 40.9 | 2100 |
| COD (mg/l) | 16.0 | 15.6 | 92 |
| BOD (mg/l) | 6.5 | 5.1 | 323 |
| total N (mg/l) | 1.25 | 0.96 | 67.0 |
| NH$_4^+$ (mg/l) | 0.03 | <0.01 | 6.9 |
| total P (mg/l) | 0.13 | 0.11 | 4.6 |

TABLE 4

| | (Garden B) | | |
|---|---|---|---|
| Analysis items | Raw water | Treated water | Average removal (g/m$^3$ · day) |
| pH | 8.0 | 8.4 | — |
| DO | 8.1 | 8.4 | — |
| suspended matters | 3.5 | 2.8 | 1353 |
| COD | 4.1 | 3.8 | 150 |

TABLE 4-continued

| | (Garden B) | | |
|---|---|---|---|
| Analysis items | Raw water | Treated water | Average removal (g/m$^3$ · day) |
| BOD | 1.5 | 1.1 | 200 |
| total N | 0.35 | 0.32 | 15.0 |
| NH$_4^+$ | 0.04 | 0.01 | 15.0 |
| total P | 0.03 | 0.02 | 5.0 |

EXAMPLE 3

A water-treatment medium (particle size range of 5–35 mm) prepared by the procedure as described in "(4) Preparation of a mechanically strengthened water-treatment medium" was packed as a 300 mm thick bed in a vertical column of a 100 mm inner diameter and a 500 mm length made of a clear acrylic resin. A stream was taken out at the downstream end of a train of aeration tanks of the public sewage treatment plant of 0 city. The raw water was allowed to stand in a sedimentation vessel. The resultant supernatant liquid was passed through the packed column at a flow rate of 200 ml/min. The test was continued for a period of three months.

The test was repeated with a higher flow rate of 500 ml/min.

The mean water analysis values are set forth in Table 5 below.

TABLE 5

| | inlet | outlet (at 200 ml/min.) | outlet (at 500 ml/min.) |
|---|---|---|---|
| pH | 6.9 | 7.4 | 7.4 |
| BOD (mg/l) | 96.8 | 2.2 | 5.7 |
| COD (mg/l) | 24.2 | 9.3 | 11.5 |
| total N (mg/l) | 12.6 | 6.9 | 14.3 |
| total P (mg/l) | 7.0 | 4.3 | 2.2 |
| suspended matters (mg/l) | 50.7 | 4.2 | 11.0 |

EXAMPLE 4

In this Example, the apparatus of the preceding Example was scaled up.

A vertical column comprising a clear acrylic resin cylinder of a 300 mm inner diameter and a 1300 mm length was charged with the water-treatment medium as used in the preceding Example 3 to contain a 400 mm thick bed of the medium therein. A stream of water was taken at a flow rate of 5 liters/min. from a brook having a width of about 6 m and a mean depth of about 0.3 m and introduced overhead into the packed vertical column and passed therethrough. This test was conducted for a period of 200 days. At the inlet and outlet, water was sampled and analyzed on 11th, 98th and 198th days, respectively. The results are set forth in Table 6 which includes also average values for the whole period.

TABLE 6

| Days | transparency (cm) | pH | suspended matters (mg/l) | BOD (mg/l) | COD (mg/l) | total N (mg/l) | total P (mg/l) |
|---|---|---|---|---|---|---|---|
| 11 days | | | | | | | |
| inlet | 20 | 6.6 | 23.0 | 14.6 | 9.0 | 4.4 | 0.10 |
| outlet | 50 | 7.0 | 7.5 | 3.5 | 7.9 | 0.61 | 0.08 |
| 98 days | | | | | | | |
| inlet | 20 | 6.8 | 26.0 | 14.0 | 11.0 | 5.0 | 0.18 |
| outlet | 65 | 7.0 | 8.7 | 5.6 | 8.7 | 0.76 | 0.12 |
| 198 days | | | | | | | |
| inlet | 20 | 6.6 | 20.6 | 11.0 | 12.0 | 5.5 | 0.27 |
| outlet | 55 | 6.8 | 10.2 | 3.8 | 6.0 | 0.80 | 0.12 |
| averages for the whole period | | | | | | | |
| inlet | 22 | 6.8 | 21.9 | 12.9 | 11.4 | 4.5 | 0.15 |
| outlet | 65.6 | 6.9 | 7.8 | 4.6 | 6.5 | 0.64 | 0.09 |

EXAMPLE 5

This Example illustrates a case where the present water-treatment medium was employed in an existing sewage treatment system installed in a superstore A so as to improve the treatment ability of that system.

The main units of the system comprised an inlet contaminated raw water pumping tank, first and second sedimentation tanks, first and second contact aeration tanks, a sedimentation vessel, a sterilization vessel and an outlet treated water discharge pumping vessel which were disposed in series being accompanied with various auxiliaries. The system was operated while returning the sludge from the first aeration tank to the preceding first sedimentation tank and returning the scum and sludge from the second aeration tank to the second sedimentation tank. The system was designed to be used by 180 persons with a sewage volume of 35.8 m³ a day.

The main objects of this Example is to more satisfactorily treat the sewage before discharging and also to substantially reduce the malodor emitted from the system.

The existing first aeration tank (a capacity of 10.68 m³) and second aeration tank (a capacity of 4.52 m³) were packed with 6.13 m³ and 2.59 m³ of a plastic contacting material, respectively. The packed contacting material in the tanks was replaced with 4.90 m³ and 2.08 m³ of a water-treatment medium according to the invention.

Further, though the existing aeration tanks had their air inlets in the side walls, the air inlets were moved from the side walls to the bottoms of the tanks and were redesigned to evenly supply air over whole the bottoms of the aeration tanks.

The water-treatment medium used in this Example was prepared by the procedure as described in "(4) Preparation of mechanically strengthened water-treatment medium", and had a particle size range of about 10–70 mm and a specific surface area of $3.8 \times 10^3$ m²/l.

Before these modifications of the system and after about three months therefrom, samples from the first pumping tank and the sedimentation vessel were analyzed. The results are set forth in Table 7 below.

TABLE 7

| | Before | After |
|---|---|---|
| Sampling Date | May 25 | September 4 |
| Sewage inlet rate (m³/day) | 21.3 | 23.0 |
| Raw water pumping tank: | | |
| pH | 5.9 | 5.6 |
| suspended matters (ppm) | 196 | 190 |
| BOD (ppm) | 387 | 260 |
| COD (ppm) | 173 | 290 |
| Sedimentation vessel: | | |
| pH | 6.9 | 7.1 |
| suspended matters (ppm) | 18 | 13 |
| BOD (ppm) | 77 | 25 |
| COD (ppm) | 48 | 19 |
| transparency (cm) | 10 | 22 |

At the same time, the malodor in the space near the closed manholes to the aeration tanks also analyzed as follows:

| | Before | After |
|---|---|---|
| ammonia (ppm) | <0.2 | <0.1 |
| methyl mercapton (ppm) | 0.011 | <0.001 |
| hydrogen sulfide (ppm) | 0.041 | 0.012 |
| malodor intensity | 230 | 42 |

The malodor intensity data were determined by a 6 membered panel in accordance with the method of Notification No. 236 of the Tokyo Metropolitan Government (the three-point comparison method with order-bags).

EXAMPLE 6

A metal work factory "K" produces captively cokes by high temperature carbonization of coal. The by-product carbonization gas is scrubbed with water. The resulting stream of washings contains various pollutants as listed below, and is very dark in color. Therefore, it is very difficult to satisfactorily treat before discharging to the environmental water.

| | |
|---|---|
| pH | 9.4 |
| COD | 6,000 mg/l |

-continued

| | |
|---|---|
| phenols | 1,600 |
| NH$_3$ | 6,000 |
| SCN$^-$ | 500 |
| S$_2$O$_3^{--}$ | 500 |
| SO$_3^{--}$ | 300 |
| H$_2$S | 300 |
| HCN | 50 |
| total S | 1,000 |
| Cl$^-$ | 1,200 |

The stream of washings is optionally subjected to de-ammoniation, and then usually is diluted with pure water or sea water by several times and treated with activated sludge to satisfy an effluent COD standard of less than 160 mg/l prior to discharging into the public water.

Experiment 1

A glass tube having an inner diameter of 20 mm and a length of 250 mm was packed with 60 ml of a granular agent (3 mm diameter and 9 mm length) prepared by the procedure as described in the above "(3) Preparation of a granular agent for treating fluids". Through the packed glass tube, a sample of the carbonization washings (raw waste water) was dripped at a rate of 50 ml/min, while continuously measuring the light transmission % of the exiting stream using a spectrophotometer (Shimazu: UV 120-02) at 350 nm.

Experiment 2

The above procedure was repeated using a sample of the activated sludge-treated washings.

Experiment 3

The procedures of the preceding Experiments 1 and 2 were repeated using an agent for water treatment described in Japanese KOKOKU No. SHO 64-6838 or a commercially available active carbon "K", respectively.

Figure 2:
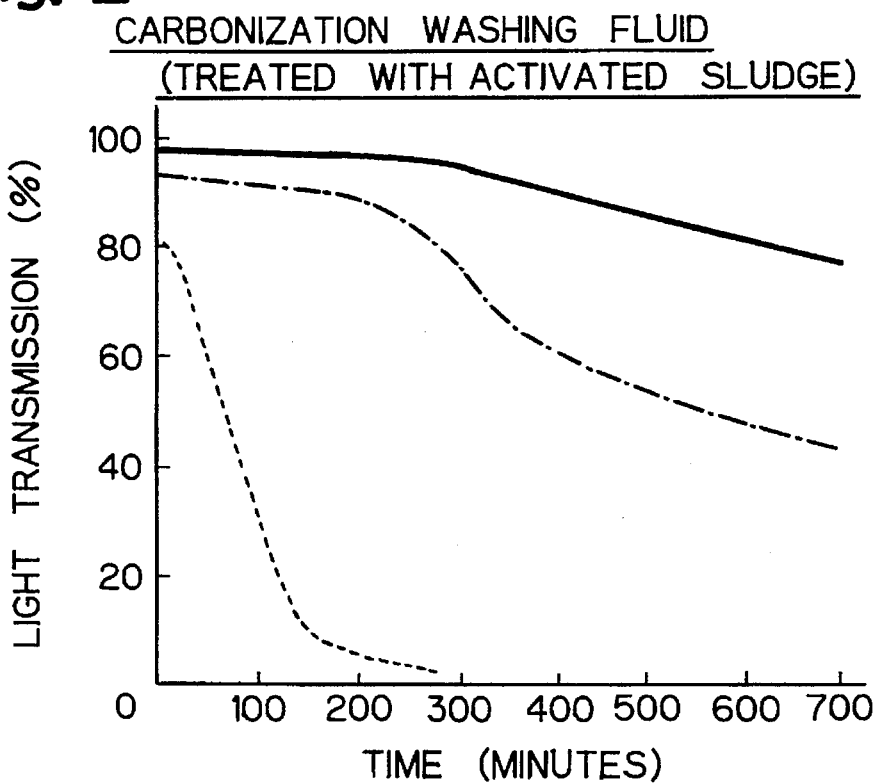
FIG. 2 is a graphic presentation similar to that of FIG. 1 except that the raw effluent has been diluted and treated conventionally with activated sludge before the treatment with the three respective agents.

The adsorbance data for the raw washings-stream are shown in FIG. 1, wherein a solid line curve (the invention), a chain-like line curve (KOKOKU No. SHO 64-6838) and a broken line curve (active carbon "K") are given. The adsorbance data for the activated sludge-treated waste water are shown in FIG. 2.

The pH and COD (mg/l) data observed after 10 minutes from the tart each of the Experiments are set forth in Table 8.

TABLE 8

| | Before | | active carbon K | | KOKOKU 64-6838 | | the invention | |
|---|---|---|---|---|---|---|---|---|
| | pH | COD | pH | COD | pH | COD | pH | COD |
| the raw washings | 4.9 | 3950 | 6.0 | 2500 | 6.2 | 2200 | 6.4 | 2000 |
| sludge-treated water | 7.5 | 30 | 7.7 | 20 | 8.0 | 19 | 8.3 | 14 |

EXAMPLE 7

A dyehouse M has an effluent water which is subjected to a flocculation treatment by addition of a flocculent and pH adjustment, and then to an activated sludge treatment. Through the effluent treatment system, the waste water becomes to satisfy the statutory standard and allowed to be discharged into the public water. When the treated water is seriously dark in the color, the water is voluntarily diluted with fresh water, for example, 4–5 times as much.

In this Example, the raw effluent water from the dyehouse M and the conventionally treated water to be discharged were tested with the various agents as in the preceding Example 6. The results are shown in FIGS. 3 and 4.

What is claimed is:

1. A composition of matter free of active carbon for use in preparation of solid media for treating fluids, which comprises, on a weight basis:

| | |
|---|---|
| humic allophane soil particulates | 40–80%; |
| binder material | 20–50%; and |
| aggregate material | 0–30%. |

2. A composition of matter according to claim 1 which comprises an aggregate material.

3. A composition of matter according to claim 2 in which said aggregate material is porous.

4. A composition of matter according to claim 3 in which said aggregate material comprises volcanic detritus.

5. A composition of matter according to claim 1 in which said binder material comprises an inorganic solid binder selected from the group consisting of cements, lime and alkali metal silicates.

6. A composition of matter according to claim 1 in which said binder material comprises an organic binder.

7. A composition of matter according to claim 6 in which said organic binder is selected from the group consisting of thermoplastic synthetic resins, thermosetting synthetic resin, tars, pitches, gum arabic, gelatin, starch and starch-derivatives.

8. A solid medium for use in treatment of fluids, which is formed from a composition of matter according to claim 1, 3, or 5.

9. A solid medium according to claim 8 which is a deodorant for use in treatment of gaseous streams, and which is prepared either by applying a slurry or easy-flowing paste to a web substrate, or impregnating a web substrate with such a slurry or paste, and then drying the wet substrate to produce a deodorant material.

10. A solid medium according to claim 8 where the fluid to be treated therewith is an aqueous effluent.

11. A solid medium according to claim 8 where the fluid to be treated therewith is air.

* * * * *